United States Patent [19]

Sanagi

[11] Patent Number: 4,632,110
[45] Date of Patent: Dec. 30, 1986

[54] MEDICAL OPERATION INSTRUMENT FOR ENDOSCOPE

[75] Inventor: Kenichiro Sanagi, Hachioji, Japan

[73] Assignee: Olympus Optical Co., Ltd., Tokyo, Japan

[21] Appl. No.: 770,955

[22] Filed: Aug. 30, 1985

[30] Foreign Application Priority Data

Sep. 28, 1984 [JP] Japan .................. 59-147110[U]

[51] Int. Cl.⁴ .................................. A61B 17/00
[52] U.S. Cl. ........................ 128/303 R; 128/305
[58] Field of Search .................... 128/305, 303 R

[56] References Cited

U.S. PATENT DOCUMENTS 1,168,115  1/1916  Rueckert ........................ 128/354
1,803,728  5/1931  Root ............................. 128/354
3,316,912  5/1967  Whitaker ....................... 128/303 R
4,178,810  12/1979  Takahashi ..................... 128/303 R
4,449,518  5/1984  Konomura et al. ............. 128/303 R Primary Examiner—Robert Peshock
Assistant Examiner—J. Hakomaki

[57] ABSTRACT

A forceps includes a flexible sheath which is to be inserted into the insertion channel of an endoscope. Sampling cups are fitted to the distal end of the sheath. A control wire is movably inserted into the sheath and connected at one end to the cups. The other end of the control wire is fitted with a control section arranged at the proximal end of the sheath. The control section effects the push and pull of the control wire, thereby opening and closing the cups. That portion of the wire which lies near to the control section is impregnated with a hardening agent to provide a hardened section.

6 Claims, 3 Drawing Figures

MEDICAL OPERATION INSTRUMENT FOR ENDOSCOPE

BACKGROUND OF THE INVENTION

This invention relates to a medical operation instrument for an endoscope (hereinafter referred to as "an endoscope operation instrument"), for example, forceps inserted into the coeliac cavity through an endoscope channel for medical operation.

The endoscope operation instrument, biopsic forceps, for example, is fitted at the proximal end with a control section containing a control slider and, at the distal end, with a medical operation cup connected to the control slider by means of a control wire. After the forceps are inserted into the endoscope forceps channel and the medical operation cup is drawn into the coeliac cavity, the cup is opened by pushing the control slider. Ordinarily, the control slider can be advanced further even after the cup is fully opened, the object being to enhance reliable opening of the cup even if the control wire itself, or the control wire channel is extended.

When, however, the operator earnestly surveys a section designated for biopsic observation (simply referred to as "a biopsic section") or considerable technique is demanded for the task of inserting the forceps into the internal organ in which said biopsic section is situated, it often happens that the operator unknowingly applies excessive force to the control slider. Also, when the tissue is sampled, the operator often tends to apply excessive force to the control slider in an attempt to completely open the cup for sampling of intact cells. When, as mentioned above, the control wire is forced excessively, namely, when the control slider is further pushed inward despite the full opening of the cup, the proximal end of the control wire, in particular, is subjected to an undue lengthwise compression. As a result, the strands constituting the control wire swell radially, presenting difficulties in effecting subtle handling of the medical operation section, what with the control wire failing to respond appropriately due to buckling or deformation.

To dissolve the above-described difficulties, a process has already been proposed which is characterized by enclosing the control wire in a tube. In this case, machining and fitting of the tube is required, leading to a higher instrument manufacturing cost. Further, the assembly of the control wire and enclosing tube constitutes too thick a mass to allow for ease of movement.

SUMMARY OF THE INVENTION

This invention has been accomplished in view of the above-mentioned circumstances, and is intended to provide the previously defined "endoscope operation instrument," characterized in that the control wire's capacity for mechanical resistance to an undue external compression force can be improved without increasing the diameter of the wire and without increasing the manufacturing cost.

To attain the above-mentioned object, this invention provides a medical operation instrument for an endoscope, comprising:

a flexible sheath introduced into an insertion channel of an endoscope;

a medical operation section set at the distal end of the sheath;

a control wire movably inserted into the sheath and connected at one end to the medical operation section; and a control section set at the proximal end of the sheath and connected to the other end of the control wire so as to effect the handling of the medical operation section by the push or pull of the control wire;

wherein the proximal end portion of the control wire, set near to at least the control section, is impregnated with a hardening agent to constitute a hardened section.

BRIEF DESCRIPTION OF THE DRAWINGS

FIGS. 1 to 3 represent an endoscope medical operation instrument according to an embodiment of the present invention, in which:

FIG. 1 is a schematic side view of the medical operation instrument inserted into the insertion channel of an endoscope;

FIG. 2 is a perspective view of the medical operation instrument; and

FIG. 3 is a longitudinal sectional view of the medical operation instrument.

DETAILED DESCRIPTION OF THE PREFERRED EMBODIMENT

Description may now be made, with reference to the accompanying drawings, of medical operation instruments for the endoscope embodying this invention.

Figure 1:
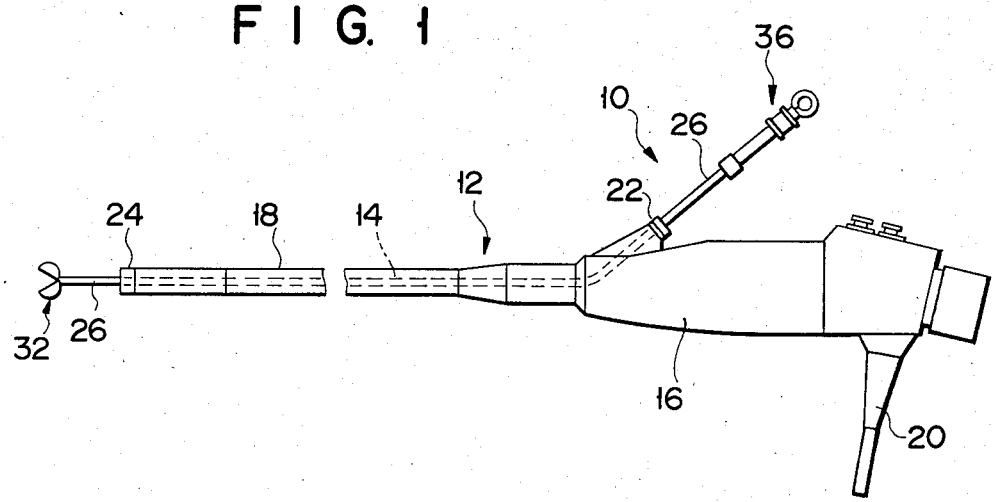

FIG. 1 shows biopsic forceps 10 inserted into the insertion channel 14 of an endoscope 12.

The endoscope 12 comprises a control section 16, an insertion section 18 extending from the control section 16, and a universal cord 20 extending from the control section 16. The control section 16 is provided with an insertion port 22. The insertion channel 14 extends from the insertion port 22 through the insertion section 18 and up to a distal end structure 24 set at the distal end of the insertion section 18.

Figure 2:
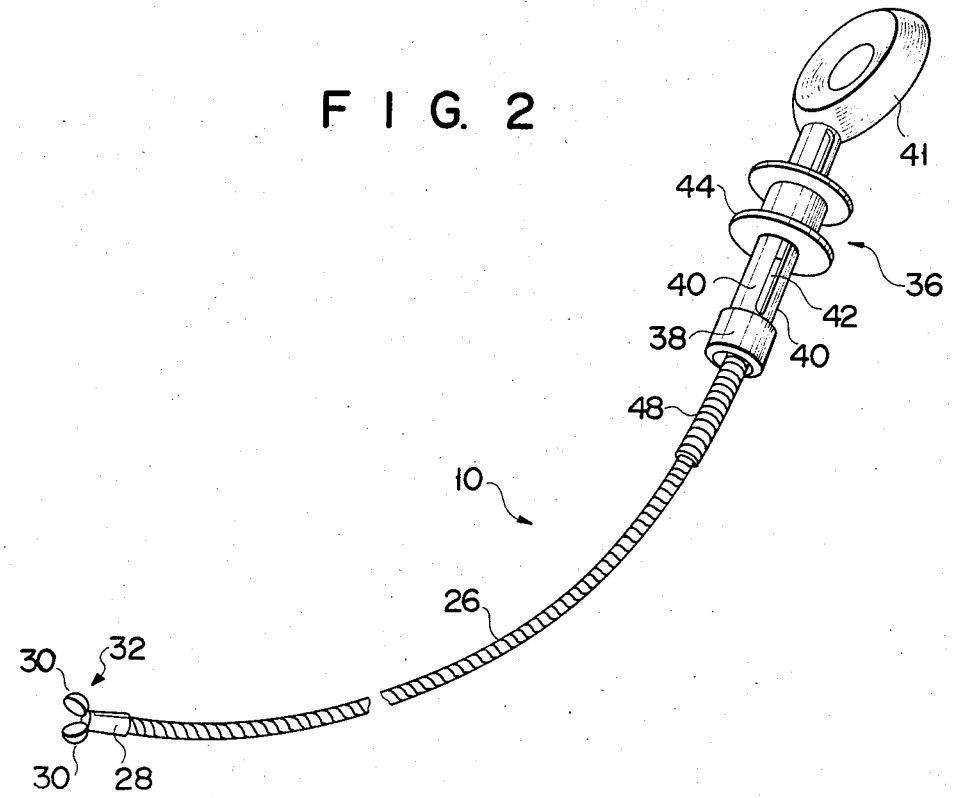
Figure 3:
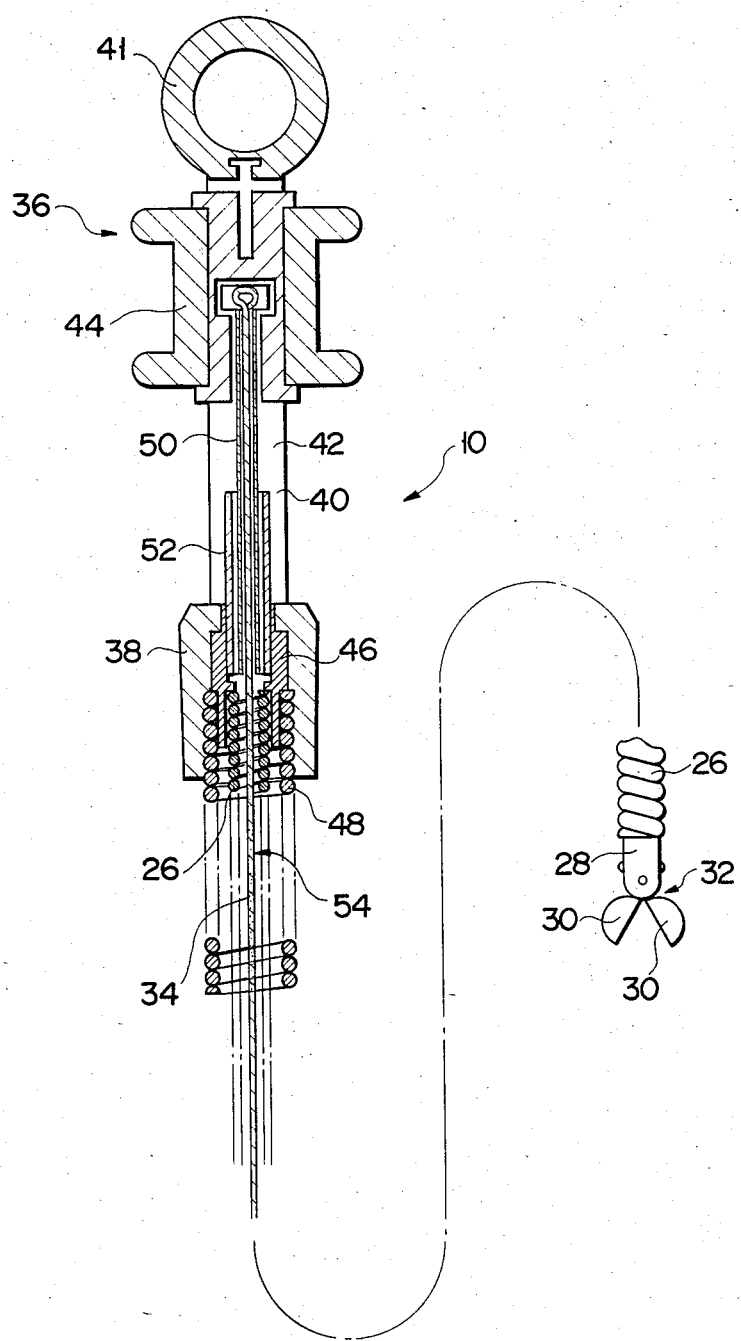

As shown in FIGS. 1 to 3, the forceps 10 includes a flexible sheath 26 narrow enough to be inserted into the insertion channel 14 of the endoscope 12. The sheath 26 is composed of a closely wound coil. The distal end of the sheath 26 is fitted with a tip 28, and the tip 28 is fitted with a pair of rotatable sampling cups 30. The paired cups 30 constitute a medical operation section 32. Movably inserted into the sheath 26 is a control wire 34 composed of a plurality of twisted strands. The distal end of the control wire 34 is connected to the paired cups 30. The cups 30 are opened or closed accordingly as the control wire 34 is pushed or pulled.

The proximal end portion of the control wire 34 is fitted with a control section 36 for effecting the push and pull of the control wire 34. The control section 36 includes a cylindrical body 38 and a pair of parallel guide rods 40 axially extending from the cylindrical body 38. Thus an elongate guide hole 42 is defined between the guide rods 40. A finger ring 41 is fixed to the outermost ends of the paired guide rods 40. A control slider 44 is fitted to the paired guide rods 40 and guide hole 42 to be slidable along the guide rods. The proximal end of the control wire 34 extends through the cylindrical body 38 and guide hole 42 and connected to the control slider 44.

The proximal end of the sheath 26 is fixed inside of the cylindrical body 38 by means of a connector 46. The outer periphery of the proximal end portion of the sheath 26 is enclosed in a sheath breakage-stopping coil type tube 48 extending from the control body 38, thereby preventing sudden bending of the sheath 26. The outer periphery of the proximal end portion of the control wire 34 is enclosed in a protective tube 50. The protective tube 50 extends through a guide tube 52 fixed to the cylindrical body 38. Therefore, that portion of the control wire 34 which passes through the guide hole 42 is prevented from buckling by the protective tube 50.

That portion of the control wire 34 which lies near the cylindrical body 38 constitutes a hardened section 54. This hardened section 54 may extend from the control section 36 to the intermediate point of the sheath 26. According to this embodiment, the hardened section 54 is formed with a length substantially equal to that of the sheath breakage-stopping coil type tube 48. The hardened section 54 is constructed by being hardened after the interstices of the strands of the control wire 34 are impregnated with a hardening agent. In the foregoing embodiment, a metal brazing agent, for example, solder is applied as a hardening agent to braze the control wire 34.

The forceps 10 constructed as described above, is applied in an actual medical operation through the undermentioned steps. First, the insertion section 18 of the endoscope 12 is inserted into the coeliac cavity. The sheath 26 of the forceps 10 is placed into the channel 14 through the insertion port 22 of the endoscope 12, and the medical operation section 32 is pushed out of the distal end structure 24. The thumb of one hand is put into the finger ring 41, while the control slider 44 is gripped by the forefinger and middle finger of the same hand. Held thusly, the control slider 44 is moved back and forth to operate the medical operation section 32 by means of the control wire 34. When the sampling cups 30 are to be opened, the control slider 44 is advanced to push the wire 34. When the cups 30 are to be closed, the control slider 44 is retracted to pull the wire 34.

The control slider 44 can be moved forward even after the cups 30 are fully opened. When, however, the control slider 44 is advanced after the cups 30 are fully opened, an excessive compression force is applied to the control wire 34. This force is weaker in the proximity of the distal end of the control wire 34 and, conversely, stronger toward the proximal end of the wire. In this embodiment, however, the proximal end portion of the control wire 34 consists of the hardened section 54. Even when, therefore, excessive compression is applied, the proximal end portion is saved from buckling and/or deformation such that the twisted strands of the control wire 34 are prevented from swelling. The hardened section 54 is formed by impregnating a hardening agent in the interstices of the strands of the control wire 34, so that the wire is prevented from being thick. Therefore, the control wire 34 can move unimpeded without catching the inside of the sheath 26 or control section 36. Further, the hardened section 54 can be formed at low cost, ensuring inexpensive production of the medical operation instruments for an endoscope.

This invention is not limited to the foregoing embodiment, being applicable to a number of variations and modifications within the scope and object of the invention. For instance, the invention is applicable not only to biopsic forceps, but also to grip forceps, just as the hardening agent may be provided not only by solder, but also by any other metal brazing agent, or adhesive.

What is claimed is:

1. An endoscope medical operation instrument for insertion into a coeliac cavity through the insertion channel of an endoscope, comprising:
   a flexible sheath inserted into the insertion channel;
   a medical operation section fitted to the distal end of the sheath so as to be inserted into the coeliac cavity;
   a control wire movably inserted into the sheath and connected at one end to the medical operation section; and
   a control section, fitted to the proximal end of the sheath and connected to the other end of the control wire, for controlling the medical operation section by pushing and pulling the control wire;
   wherein at least the other end portion of the control wire, positioned near to the control section, is impregnated with a hardening agent to provide a hardened section.

2. The endoscope medical operation instrument according to claim 1, wherein said hardening agent is a metal brazing agent.

3. The endoscope medical operation instrument according to claim 2, wherein said metal brazing agent is solder.

4. The endoscope medical operation instrument according to claim 1, wherein said hardening agent is adhesive.

5. The endoscope medical operation instrument according to claim 1, wherein said control section includes a cylindrical body, a guide section extending from the cylindrical body and a control slider movably fitted to the guide section; and the other end of said control wire passes through the cylindrical body and is fixed to the control slider.

6. The endoscope medical operation instrument according to claim 5, wherein said control section includes a control wire breakage-stopping tube which extends from the cylindrical body toward said one end of the control wire and surrounds the other end of the control wire, and said hardened section extends from the control section to within the neighborhood of the extended end of the control wire breakage-stopping tube.

* * * * *